United States Patent [19]

Duffett

[11] Patent Number: Plant 5,714

[45] Date of Patent: Apr. 8, 1986

[54] CHRYSANTHEMUM PLANT NAMED DORADO

[75] Inventor: William E. Duffett, Salinas, Calif.

[73] Assignee: Yoder Brothers, Inc., Barberton, Ohio

[21] Appl. No.: 636,569

[22] Filed: Aug. 1, 1984

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Dorado characterized as to uniqueness by the combined characteristics of flat capitulum form, decorative capitulum type, deep yellow ray floret color, diameter across face of capitulum ranging from 8.5 to 9.0 cm. at maturity, uniform nine week flowering response, tall plant height when grown single stem, 20 to 25 cm. peduncles on open, normally terminal sprays, 13° C. minimum temperature tolerance for initiation and development of flowering buds under a 12 hour continuous dark period, and high leaf and flower durability.

3 Drawing Figures

The present invention comprises a new and distinct cultivar of *Chrysanthemum morifolium,* Ramat., named Dorado.

Dorado is a product of a planned breeding program which had the objective of creating new chrysanthemum cultivars having low temperature tolerance for cut spray mum programs, with decorative capitulum type, yellow ray floret color, eight to nine week flowering response, and the ability to produce commercially acceptable quality in year round programs. Such traits in combination were not present or needed improvement in previously available commercial cultivars.

Dorado was identified as 81762016 and was originated from a cross made by William E. Duffett in a controlled breeding program in Salinas, Calif. in 1980. The female parent was Win, identified as 781574004, and disclosed by U.S. Plant Pat. No. 5,108. The male parent of Dorado, identified as 78759001, was an unnamed seedling.

Dorado was discovered and selected as one flowering plant within the progeny of the stated cross by William E. Duffett on Nov. 6, 1981 in a controlled environment in Bogota, Colombia.

The first act of asexual reproduction of Dorado was accomplished when vegetative cuttings were taken from the initial selection in February 1982 in a controlled environment in Bogota, Colombia by a technician working under formulations established and supervised by William E. Duffett through Fernando Jaramillo.

Horticultural examination of selected units initiated March 1983 has demonstrated that the combination of characteristics as herein disclosed for Dorado are firmly fixed and are retained through successive generations of asexual reproduction.

Dorado has not been observed under all possible environmental conditions. The phenotype may vary significantly with variations in environment such as temperature, light intensity, and day length. The following observations, measurements and comparisons describe plants grown in Bogota, Colombia under greenhouse conditions which approximate those generally used there in commercial practice.

The following traits have been repeatedly observed and are determined to be basic characteristics of Dorado which in combination distinguish this chrysanthemum as a new and distinct cultivar:

1. Flat capitulum form.
2. Decorative capitulum type.
3. Deep yellow ray floret color.
4. Diameter across face of capitulum ranging from 8.5 to 9.0 cm. at maturity.
5. Uniform nine week photoperiodic flowering response to short days.
6. Long peduncle length, ranging from 20 to 25 cm.
7. Tall plant height, requiring one long day week prior to short days to attain a flowered plant height of 90 to 105 cm. for year around flowering.
8. Low temperature tolerance of 13° C. for initiation and development when grown in single stem cut spray programs with a continuous dark period of 12 hours.
9. High leaf and flower durability with high shipping and keeping quality.

The accompanying photographic drawings show typical inflorescence and foliage characteristics of Dorado with the colors being as nearly true as possible with illustrations of this type. Sheet 1 is a color photograph of Dorado grown as a single stem cut spray. Sheet 2 is a black and white photograph of three views of the inflorescence of Dorado. Sheet 3 is a black and white photograph showing the upper surface and under surface of leaves of Dorado at three stages of development (mature, intermediate and immature).

Of the many commercial cultivars known to the present inventor, the most similar in comparison to Dorado is Yellow Polaris. Reference is made to attached Chart A which compares certain characteristics of Dorado to those same characteristics of Yellow Polaris. Dorado develops deeper yellow color, has a taller plant height, and is two weeks faster in response under short photoperiods. The type, form, peduncle of length, low temperature tolerance, and inflorescence diameter of Dorado are similar to those same characteristics of Yellow Polaris.

In the following description, color references are made to The Royal Horticultural Society Color Chart. The color values were determined between 11:15 A.M. and 11:30 A.M. on Dec. 27, 1983 under 380 footcandle light intensity at Salinas, Calif.

Classification:

*Botanical.*—*Chrysanthemum morifolium,* Ramat., cv Dorado.

*Commercial.*—Decorative cut spray mum.

I. Inflorescence:

A. *Capitulum.*—Form: Flat. Type: Decorative. Diameter Across Face: 8.5 to 9.0 cm.

B. *Corolla of ray florets.*—Color (General Tonality From A Distance of Three Meters): Deep yellow. Color (upper surface): 9A, 9B. Color (under surface): 9C. Shape: Oblong. Rays roll laterally.

C. *Corolla of disc florets.*—Color (mature): 2A. Color (immature): 1A.

D. *Reproductive organs.*—Androecium: Present disc florets only; scant pollen. Gyneocium: Present both ray and disc florets.

II. Plant:

A. *General appearance.*—Height: Tall; 90 to 105 cm. as a flowering plant from a rooted cutting, with seven long days for year around flowering maintaining a minimum nightly 12 hour continuous dark period.

B. *Foliage.*—Color (upper surface): 137A. Color (under surface): 147B. Shape: Shallow, narrow lobed with slight serration.

CHART A

COMPARISON OF DORADO AND YELLOW POLARIS

| CULTIVAR | RAY FLORET COLOR | CAPITULUM FORM AND TYPE |
|---|---|---|
| DORADO | DEEP YELLOW | FLAT DECORATIVE |
| YELLOW | YELLOW | FLAT |

CHART A-continued

COMPARISON OF DORADO AND YELLOW POLARIS

| POLARIS | | DECORATIVE |
|---|---|---|
| CULTIVAR | SPRAY FORMATION | DIAMETER ACROSS FACE OF CAPITULUM |
| DORADO | 20 to 25 cm. PEDUNCLES | 8.5 to 9.0 cm. |
| YELLOW POLARIS | 20 to 25 cm. PEDUNCLES | 8.0 to 9.0 cm. |

| CULTIVAR | PLANT HEIGHT | FLOWERING RESPONSE PERIOD | LOW TEMPERATURE TOLERANCE |
|---|---|---|---|
| DORADO | TALL 90 to 105 cm. | 9 WEEKS | 13° C. |
| YELLOW POLARIS | TALL 90 to 100 cm. | 11 WEEKS | 13° C. |

COMPARISONS MADE OF PLANTS GROWN AS SINGLE STEM CUT SPRAY MUMS WITH 7 LONG DAYS IN BOGOTA, COLOMBIA

I claim:

1. A new and distinct plant of *Chrysanthemum morifolium,* named Dorado, as described and illustrated, and particularly characterized as to uniqueness by the combined characteristics of flat capitulum form; decorative capitulum type; deep yellow ray floret color; diameter across face of capitulum ranging from 8.5 to 9.0 cm. at maturity; uniform nine week flowering response; tall plant height when grown single stem; 20 to 25 cm. peduncles on open, normally terminal sprays; 13° C. minimum temperature tolerance for initiation and development of flowering buds under a 12 hour continuous dark period, and high leaf and flower durability.

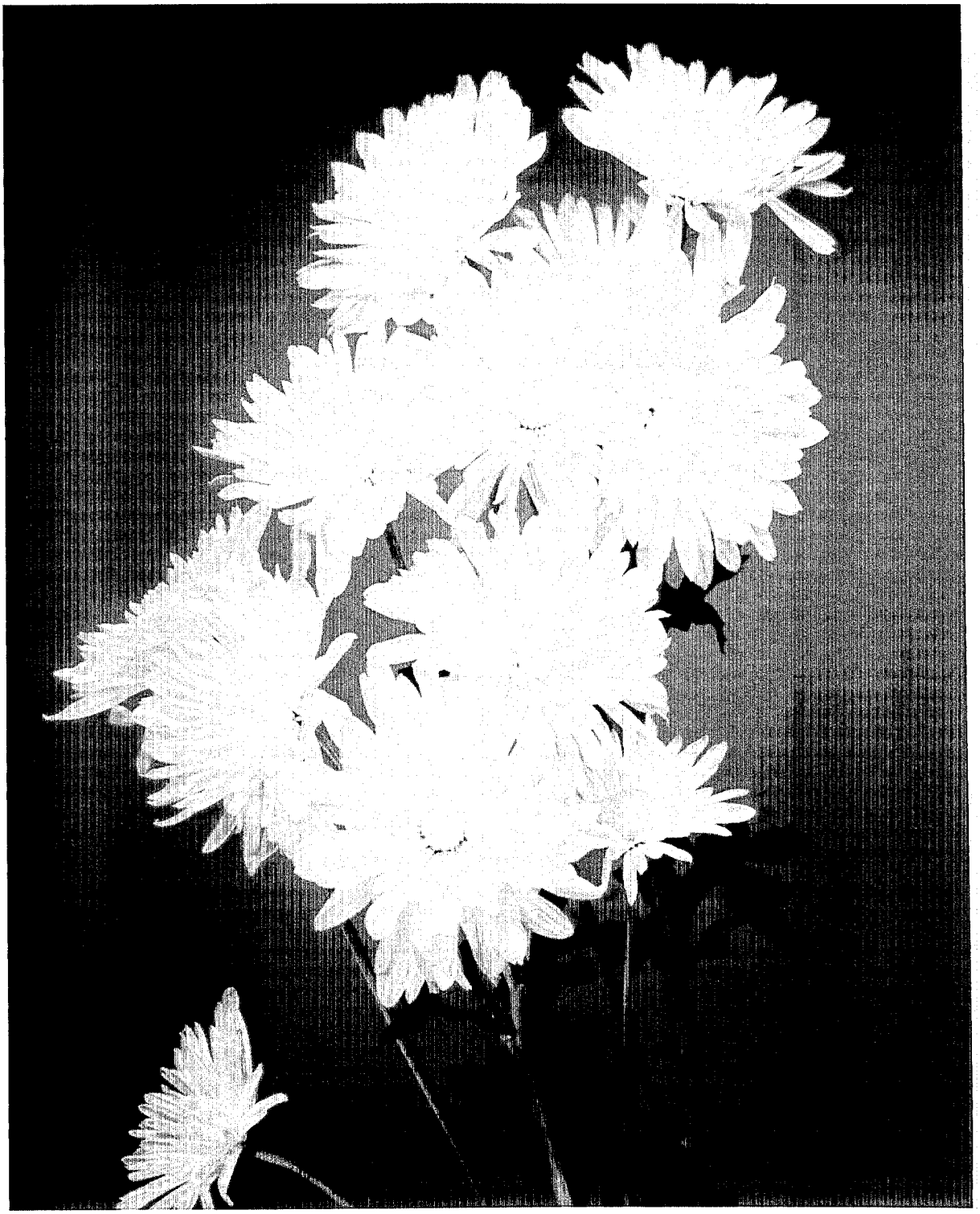

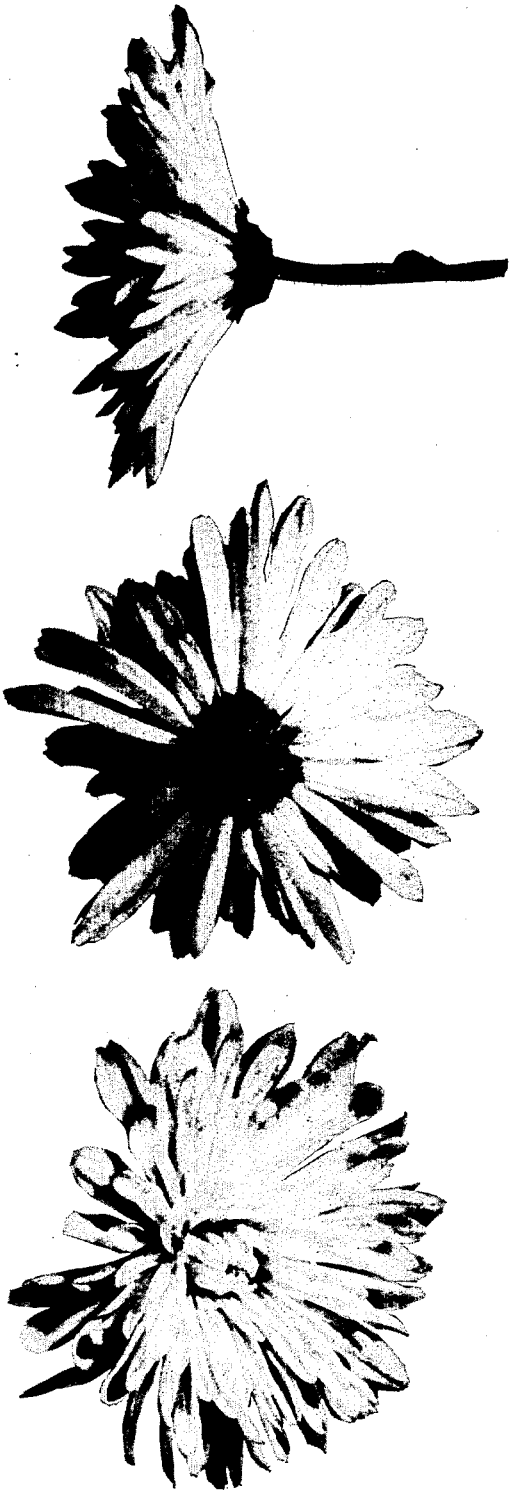

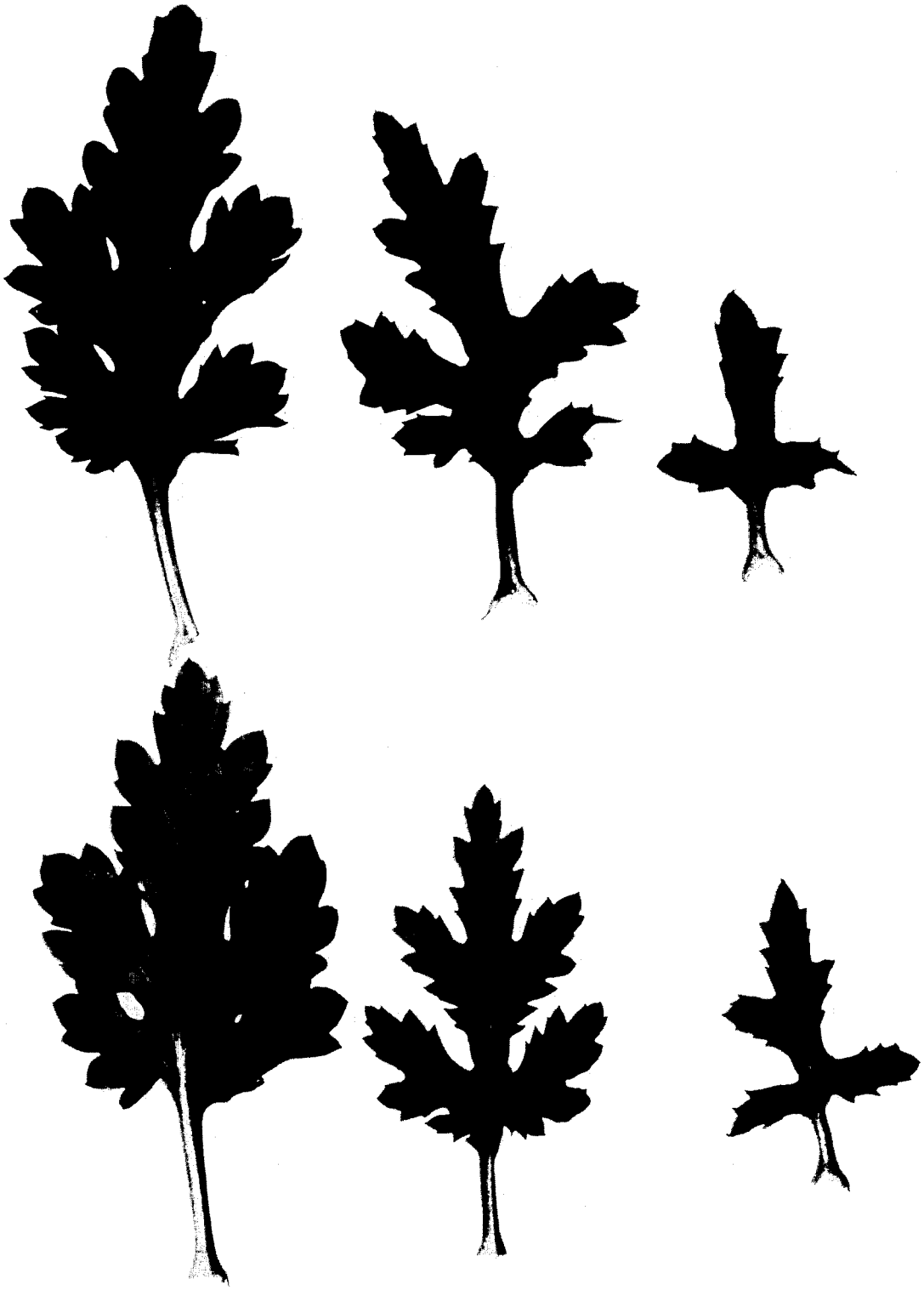

* * * * *